United States Patent [19]

Jenkins et al.

[11] Patent Number: 5,466,601
[45] Date of Patent: Nov. 14, 1995

[54] SELECTIVELY REMOVING EMBEDDED LINT PRECURSORS WITH CELLULASE

[75] Inventors: Terry L. Jenkins, Columbus; Michael L. McAbee, Cataula, both of Ga.; Joe W. Richardson, Jr., Alexander, Ala.

[73] Assignee: Exxon Chemical Patents Inc., Linden, N.J.

[21] Appl. No.: 188,051

[22] Filed: Jan. 26, 1994

Related U.S. Application Data

[63] Continuation-in-part of Ser. No. 866,828, Apr. 10, 1992, abandoned.

[51] Int. Cl.$^6$ .............................. C12S 11/00; C12S 3/04; C09B 67/00; D01B 1/04
[52] U.S. Cl. .............................. 435/263; 435/277; 19/40; 8/401; 8/112
[58] Field of Search .............................. 435/263, 277, 435/209; 19/40; 8/112, 401

[56] References Cited

U.S. PATENT DOCUMENTS

| | | | |
|---|---|---|---|
| 4,343,070 | 8/1982 | Wade et al. | 19/40 |
| 4,822,516 | 4/1989 | Suzuki et al. | 252/174.12 |
| 4,832,864 | 5/1989 | Olson | 252/174.12 |
| 5,006,126 | 4/1991 | Olson et al. | 8/401 |
| 5,310,424 | 5/1994 | Taylor | 8/190 |

FOREIGN PATENT DOCUMENTS

| | | | |
|---|---|---|---|
| 5248236 | 12/1977 | Japan . | |
| 5854082 | 3/1983 | Japan | D06M 16/00 |
| 450365 | 2/1992 | Japan | D06M 11/00 |

OTHER PUBLICATIONS

Biosis Abstract 80:38984. White et al *J. Cell Biology* 83, 1979.

*Primary Examiner*—William H. Beisner
*Assistant Examiner*—T. J. Reardon
*Attorney, Agent, or Firm*—John J. Mahon

[57] ABSTRACT

The present invention comprises a three step process that selectively removes embedded cellulose lint precursors from a cotton fabric with a cellulase solution during a continuous fabric manufacturing process. The cellulase solution, applied continually, travels in a finite, limited path and digests fibrils, forming embedded lint precursors, from the fabric. Undigestable fibrils, located outside the path travelled by the cellulase, remain undamaged by the cellulase. After the fabric's first wash, no appreciable linting is observed on the surface thereof and the fabric retains at least about 90% of its strength. Further, the process produces fabrics which do not exhibit commercially unacceptable yellowing from the action of the cellulase upon the cellulose.

16 Claims, No Drawings

SELECTIVELY REMOVING EMBEDDED LINT PRECURSORS WITH CELLULASE

CROSS REFERENCE TO RELATED APPLICATION

This is a continuation-in-part of application Ser. No. 07/866,828 filed on Apr. 10, 1992, now abandoned.

BACKGROUND OF THE INVENTION

It is well known that the application of cellulase to cotton fabrics results in the unwanted destruction and weakening of cellulosic fibers. The natural propensity of cellulase to hydrolize cellulose can easily cause cellulose to leave entire regions of fabric weakened, altered and undesirable for use. Hydrolysis of cellulose by cellulase also forms sugars which have the potential of yellowing when exposed to heat during drying.

Consequently, previous inventors have found limited ways of applying cellulase to cellulosic fibers. Japanese Patent No. Sho S2-48236, for instance, immerses a fabric in a batch process where an enzyme solution is recirculated for a short time. The process imparts mild, hygroscopic properties and smoothness to a fabric. Applying cellulase in such manner, however, weakens the fabrics from 15% to 50%. Japanese Patent No. Sho 58-54082, Kurashiki pretreats a fabric with a swelling agent, neutralizing the fabric before applying cellulase. The swelling agent, imparting strength to the fabric, nevertheless appreciably weakens the fabric. U.S. Pat. No. 4,343,070 Wade teaches the use of cellulase applied with a wetting agent for short periods of time in order to remove lint from cotton seed. The cellulase is applied "subjectively" however, and the patent does not teach any conditions which will delint fabrics without undesirable strength loss.

U.S. Pat. No. 4,822,864 (Olson), by contrast, teaches use of a batch process where clothing is intentionally damaged with cellulase during application. The fabric is contacted with the cellulase solution and agitated, and the cellulase enzyme cleaves cellulose from the surface of the fabric and indigo dye to give a stone washed look. The process is used to modify denim where such a "stone washed" look is often desired.

As the use of open end yarn has increased, the need to modify cellulosic fabrics without the destruction, discoloration and weakening of fibers has also increased. For years, most cotton-comprising fabric was produced using ring spun yarn, a high quality yarn which is tightly twisted with little fraying of individual fibers. Open end spinning technology, however, has enabled manufacturers to use less expensive, lower grades of cotton to develop open end yarn. Today, only the finest garments are made from ring spun yarn.

The increased use of fabrics made from open end yarn, particularly cotton towels, has demonstrated that open end fabrics lint substantially more than ring spun fabrics. Unlike ring spun yarn, open end yarn contains an appreciable number of protruding fibrils, or embedded lint precursors. Ordinarily, these embedded lint precursors remain with the open end yarn after the manufacturing of a cotton fabric. During the first wash, however, these precursors break free, entangle, and form lint.

Accordingly, "embedded lint precursors" as is used herein, means those fibrils that exist in the yarn, which when broken off, form lint. "Lint" as is used herein, means the entanglement of lint precursors ordinarily occuring at the first wash. "Delinting" means a process of removing embedded lint precursors with cellulase during the manufacturing process.

The embedded lint precursors are not the only fibrils that break free from an open end fabric. "Pilling" for instance, ordinarily refers to fibrils that are surface entangled during the repeated wear and washing of a fabric. Pilling, however, results from the entanglement of ingrained non-protruding cellulosic fibrils that resist being removed during the first wash, not the protruding embedded cellulosic fibrils. Similarly, entire cotton fibers may break free from a fabric by the effect of a swelling agent or repeated use. Such removed cotton fibers, however, are not the removed protruding lint precursors that are refered herein as lint.

The customary ways of applying cellulase to cellulosic fibers have prevented consumers from enjoying towels that do not exhibit an appreciable amount of lint after a first washing. Manufacturers, receiving numerous complaints from consumers about the appearance of lint on cotton towels when the towels are first washed by a consumer, have used prior methods in vain trying to delint fabrics effectively. The use of a swelling agent, although reducing strength loss, nonetheless produces undesirably weak fibrils and inadequately removes embedded lint precursors. Similarly, the application of cellulase to a fabric that is agitated and circulated to produce a "stone wash" appearance, destroys desired fibrils in fabrics that are not ordinarily stone washed and can give increased amounts of lint and excessive strength loss.

It has now been discovered, contrary to ordinary custom and usage, that cellulase may be applied, during a continuous manufacturing process, to selectively remove embedded lint precursors without causing the fabric to lose an appreciable amount of strength. It has further been discovered that cellulase may be applied without pretreating the cotton fabric with a swelling agent.

It is the principal objective of this invention to selectively digest unwanted fibrils that form embedded lint precursors in cotton fabrics while obtaining a strength loss of less than 10%. It is another objective of the invention to remove embedded lint precursors from cotton fabrics without creating an unaccepatable yellowing.

SUMMARY OF THE INVENTION

The present invention comprises a three step process for selectively removing embedded lint precursors with cellulase from a cotton fabric during a continuous manufacturing process. First, a dilute cellulase solution is prepared. Second, the cellulase is applied continually onto a fabric for a limited period of time such that it travels in a finite, limited path to the protruding embedded lint precursors. Third, embedded lint precursors are digested from the fabric. Undigestable fibrils, located outside the path travelled by the cellulase, remain undamaged by the cellulase.

The cellulase is generally applied a single time during a towel manufacturing process prior to a finishing stage. Cellulase, however, may also be applied a second time during a finishing stage at a lower concentration. After the fabric's first wash, no appreciable linting is observed on the surface of the fabric and the fabric retains at least about 90% of its untreated strength as determined by a suitable strength test, e.g. a Scott test. Further, the process produces fabrics which do not exhibit a visually unacceptable yellowing.

The improved fabric is not pretreated with a swelling agent. This enables the consumer to enjoy a fabric whose original natural strength is virtually intact, not an inferior fabric weakened and manipulated with a swelling agent.

DETAILED DESCRIPTION OF THE INVENTION

The present invention comprises a process for applying cellulase during a continuous manufacturing process wherein embedded lint precursors are selectively digested with cellulase. The process creates fabrics that retain at least about 90% of their strength. The process also effectively removes embedded lint precursors and does not exhibit linting after the first wash. The process further produces fabrics that are not yellowed to a degree ordinarily considered unacceptable by consumers.

The cellulase solution, containing a conventional, non-ionic surfactant, may be prepared at various concentrations. Preferably, a cellulase solution having a concentation about 0.3% based on the total weight of the solution is used. Preferred cellulases include Cellusoft L of NOVO Nordisk or Rapidase GL of International Biosynthetics, Inc. (IBIS), although any commercially available cellulase enzyme may be used. Cellusoft L is reported by its manufacturer to have an activity of 1,500 Novo Cellulase Units. One Novo Cellulase Unit is the amount of enzyme which, under certain Novo standard conditions, reduces carbohydrates equivalent to 1 μmol glucose per minute. Rapidase GL is reported to have a cellulose activity of about 103–112 CCU per gram. The fibrils may also be treated with a cationic softener, although this is not used in a preferred embodiment.

Being that the effective distance of the cellulase is defined by the concentration of the cellulase solution, the pH of the solution, the time the solution is applied, and the temperature of the solution, a cellulosic fabric that is to be improved with the present process contains both digestible fibrils and nondigestible fibrils prior to being treated. The digestible fibrils are those fibrils protruding from a fabric's fibers which are within the path travelled by a sufficiently high concentration of cellulase that they will be in contact with the cellulase for a sufficiently long period at the proper pH to be digestable thereby. The non-digestible fibrils are those fibrils located outside the path travelled by the cellulase, such as ingrained fibrils. The cellulase, travelling in a fixed, finite path, selectively digests the protruding embeddded lint precursors while leaving non-protruding ingrained fibrils uneffected.

Accordingly, the cellulase solution, held in a storage container, flows through an applicator onto the fabric. The cellulase is applied continuously to a bath through which the fabric travels during one stage of its manufacturing procedure. Preferably, the cellulase solution has a concentration of at least about 0.1–0.6% based on the total weight of the solution and, is maintained in contact with the fabric applied for a period ranging from about 2 hours and up to a maximum for very dilute cellulase solutions of a few days, e.g. over a weekend. During application of the cellulase, the fabric is neither agitated nor circulated. The temperature of the solution is preferably at least about 60° F., preferably about 120° to 130° F., and the dwell temperature, the temperature maintained during the application of the cellulase is at least about 40° F., preferably about 80° to 90° F. The solution pH will bepend upon the specific cellulase utilized (certain cellulases are more effective at specific pH's) but will generally be in the range of about 4 to 6, preferably about 5.

The present invention is used in widely known processes with the following steps: formation, preparation, dyeing, and finishing steps with staging periods exist between such steps. During formation, the yarn is generally first treated with a sizing agent. Starch, polyvinyl alcohol, carboxymethyl cellulose, waxes and acrylic binders are examples of typical sizing chemicals. The yarn is then knitted or woven into a fabric. The fabric is not pretreated with a swelling agent.

The preparation step, comprising the substeps of desizing, scouring and bleaching, involves the treatment of the formed fabric with chemicals. The chemicals are added by a chemical feed means to a saturator where the chemical is brought into contact with the formed fabric. The formed fabric can be either woven or knitted and the use of a woven towel is preferred. The preferred towel has a ground of 100% cotton with a pile of about 100% cotton, although the ground may be partially polyester. The "ground" is that part of the towel which provides strength to the towel and serves as a substrate for the pile. The "pile" is the non-weight bearing portion of the fabric which is woven through the ground which provides softness and absorbency to a towel. The pile can have various styles such as sheared, non-sheared, or flat.

During the desizing stage of the preparation step, any lubricants and sizing chemicals applied prior to the weaving or knitting of the yarn are removed by the application of chemicals such as amylase, hot water, caustic soda (NaOH), surfactants, and alkaline hydrogen peroxide. The chemicals are applied in a saturator bath which generally ranges from about 60° to 130° F. The desizing agent is often a combination of hot water and a surfactant. The saturated fabric is allowed to stand with the desizing chemicals for a "holding period" sufficiently long to accomplish the desizing. The holding period varies from 15 minutes to 2 hours, or several days. The fabric is held in equipment such as a "J-box." The J-Box provides sufficient heat, usually between 90° and 110° F. to enhance the activity of the agents. The chemicals are washed out after the termination of the holding period.

Preferably, the fabric is treated with cellulase during the desizing step for 12 hours. After the cellulase has been applied to the fabric, the digested lint precursors are removed. The fabric completes its manufacturing process. Subsequently, the fabric does not produce an appreciable amount of lint during the first wash. The fabric also does not yellow undesirably, and the fabric retains more than 90% of its strength.

During the scouring stage of the preparation step, chemicals such as sodium hydroxide, soda ash, phosphates, silicates, surfactants, and solvents, are added in conditions similar to the conditions of lay time and temperature as is the desizing stage. The scouring stage is not a preferred stage to apply cellulase, being that most cellulases are inactive under such conditions. Nevertheless, it is possible that a neutral cellulase could be applied in a reduced alkali application or even in the washing operation to remove the scouring materials, if the pH is sufficiently reduced as in the last stage of a multistage washing system. During the bleaching stage, the chemicals such as hydrogen peroxide, sodium hypochlorite and sodium chlorite are added to complete the cleaning process, under conditions similar to the lay time and temperature in the desizing stage.

During the finishing stage, wet-on-wet or wet-on-dry softeners as well as other additives, are added to the fabric to achieve desired physical performance and luster. In a preferred embodiment, a second very light application of cellulase is made during the finishing stage. The concentration of the cellulase solution applied during the finishing stage is relatively lower than the concentration of the cellulose solution applied during the desizing stage. Prior to the finishing stage, the fabric may undergo a dyeing stage. The dyeing stage, however, is not a preferred stage for applying the cellulase.

Examples 1–17 illustrate the advantages of the present invention. The results of the 17 separate tests illustrate conditions which indicate appropriate cellulase application location(s) in the manufacturing process. The 13 Comparative Examples that failed to achieve the desired results are included for comparison. The examples are provided for the purpose of illustration and are not meant to be limiting. In the examples all values expressed in parts or percents are by weight unless otherwise indicated.

Unless otherwise stated, the linting results expressed in the Examples are based on the inspection of the towel after one home laundering, i.e. the site of maximum linting. "Acceptable linting peformance" herein means minimal to no linting observed upon a visual inspection of the towels after one home laundering. Unless otherwise stated, the Examples are carried out in a continuous operation in which the fabric is continuously pulled through a saturator into which chemicals and water are continuously added and the fabric continuously enters and exits a J-box after an initial 40–60 minute time period to fill the J-box and establish a lay time as dictated by the amount of fabric the J-box will hold and the level to which it is filled.

EXAMPLE 1

Dry, loomstate toweling, i.e. before any desizing or other preparative procedures are performed, is saturated wet on dry to 90–120% wet pick up with a cellulase and surfactant solution. The cellulase used is Cellusoft L. The surfactant used is a conventional non-ionic desizing surfactant at a concentration of 0.25% of bath. The surfactant composition is not critical as long as it causes the size film and fabric to be thoroughly and uniformly wetted out and does not deactivate the cellulase enzyme. The cellulase solution is constantly maintained at 60° to 80° F. and the pH controlled within the range of 4.8 and 5.3 by addition of acetic acid and soda ash as necessary. A bath concentration of 0.1–0.15% cellulase is maintained by an initial charge and continuous additions therefter based on the amount of liquid carried out of the saturator by the continously running toweling fabric. After saturation of the fabric as stated above, the fabric is held in pits (bins) for 2–3 days (over a week-end) at about 60°–80° F., not being allowed to dry out. Thereafter, the fabric continues through the normal preparation stage, is dyed and finished with no additional treatment.

The fabric is formed into toweling and the resulting towels showed no problem with linting after one home laundry. Furthermore, the towels showed no yellowing as determined by a visual inspection, and less than 10% loss of strength, both as compared to untreated fabric.

EXAMPLE 2

The procedure of Example 1 is repeated except that during the finishing stage of the manufacturing process, an additional cellulase treatment is made by the incorporation into the finishing bath chemicals of 0.02–0.04% Cellusoft L on the weight of the fabric. The dwell (lay) time prior to drying of the fabric ranged from 0 to 60 minutes. The finished goods are then dried at 275°–325° F. in a continuous loop dryer over a 15–30 minute time period.

The towel exhibits excellent linting performance and less than 10% strength loss. No yellowing is observed by a visual comparison with an untreated towel.

EXAMPLE 3

The procedure of Example 1 is repeated with the following changes: the cellulase solution is constantly maintained at about 110°–120° F. and the pH is maintained in a range from about 4.8 to 5.3. A bath concentration of 0.25–0.35% is maintained. After saturation in Example 1, the fabric is held in pits (bins) for 2 to 6 hours at 90°–110° F. prior to subsequent processing. The towel is not treated with additional cellulase enzyme in finishing.

The towel exhibits excellent linting performance, no notable strength loss, no yellowing, and even reduced lint on the final product being sold after one home laundry.

EXAMPLE 4

The procedure of Example 3 is repeated with the addition of a second cellulose treatment as part of the finishin stage. Softener in a concentration sufficient to allow about 0.4–0.6% softener solids on the weight of the towel is provided in the finishing bath and Cellusoft L is also added in sufficient concentration to allow about 0.02%–0.04% cellulase on the weight of the towel.

The resulting towel exhibits even less linting after one home laundry than does the towel of Example 3.

EXAMPLE 5

The procedure of Example 1 is repeated except with the following changes: the cellulase solution is constantly maintained at 90°–120° F. and the pH is controlled within the range of 4.8 and 5.3. A bath concentration of 0.3–0.6% Cellusoft L is maintained. After saturation of the fabric to 90–120% wet pick-up on the weight of the fabric, the fabric is held in a J-Box at 90°–120° F. for 40–60 minutes. After the lay time in the J-Box, the fabric is pulled through a washing operation at 130°–150° F. to remove the cellulase. Subsequent processing includes continuing the preparation process (alkali scouring, bleaching), dyeing and finishing with no further cellulase treatment in finishing.

The fabric processed as described has good linting performance and minimal lint is carried on the final product to the consumer. There was not yellowing and no notable strength loss.

EXAMPLE 6

The cellulase solution of EXAMPLE 1 is prepared. During the desizing stage, the solution is applied continously to a cotton fabric for 24.0 hours. The solution treatment temperature and the dwell temperature are those in Example 1.

The fabric retains 91.3% of its strength. The yellowing is minimal, and the towel linting performance is fair to good.

EXAMPLE 7

The procedure of Example 5 was repeated with the following addition: the toweling is finished using 0.2–0.6% softener solids on the weight of the towel and 0.035–0.15% Cellusoft L on the weight of the towel. After the finishing chemicals application, lay time before drying ranges from 0 to 60 minutes. Toweling is dried at 275°–325° F. over a 15–30 minute time period in a forced hot air loop dryer.

Towels processed in this manner exhibit excellent linting performance and minimal lint is carried forth on the final product. No yellowing or notable strength loss is observed.

EXAMPLE 7A and 7B

In Example 7A, a fabric is treated only once and that is as part of finishing it. The moisture content of the fabric is adjusted in an open-width dip nip operation using a double (mangle set-up) so that a positive exchange of finish liquor is accomplished. The fabric is immersed in a finishing solution (bath) maintained at pH 3.8–4.2 containing 1–3% softener solids and 0.5–0.8% Cellusoft L cellulase at a temperature of 80°–110° F. and squeezed (nipped) to 15–30% exchange or 0.15–0.9% softener solids on the fabric and 0.075%–0.2% Cellusoft L weight of the fabric (towel). The finished (wet) fabric is allowed to lay (dwell) in boxes at 80°–100° F. for various times ranging from about 0 to 60 minutes and then dried at 275°–325 ° F. in a hot air loop dryer over a 15–30 minute time period. The cellulase is not washed out until the fabric is first laundered. Rather, it is inactivated by the heat of the hot air loop drier which reached temperatures of 275°–325° F.

For Example 7B, the procedure of 7A is repeated except the cellulase enzyme Rapidase GL is substituted for Cellusoft L. The results were the same for each example and are detailed below.

The toweling processes above, in both Example 7A and 7B, perform acceptably on linting tests, that is, minimal or no linting observed upon visual inspection of the towels after one home laundering. No significant strength loss is noted and there is no evident yellowing, particularly on the medium to dark shades. No substantial difference in performance is observed based upon the lay time because the drying is over an extended period.

EXAMPLE 8A and 8B

In example 8A, the procedure of Example 7A is repeated with the following changes: the softener solids on the towel (fabric) are reduced to 0.2–0.6% and cellulase on the towel is at an amount of 0.035–0.08%. The lay time is 0–60 minutes.

For example 8B, the procedure of Example 7A is repeated except that Rapidase GL is used.

These procedures are performed with three different fabrics, i.e. white, pastel and dark colored towelling. The towelling processed in this manner performs acceptably for linting performance although some lint was carried forth to the final product. No significant strength loss was noted. During numerous trial and production runs, the towels showed no yellowing for any of the towels.

EXAMPLES 9A, 9B and 9C

In Example 9A, during a three stage prepare, Cellusoft L is applied to a fabric in the last wash box after bleaching so that the fabric is saturated uniformly with 0.25–0.4% Cellusoft L on the weight of the fabric (towel) at a pH range of 4.8 to 5.3 and temperature of 90°–130° F. After saturation of fabric by the cellulase solution, the fabric is allowed to lay (dwell) for about 2–4 hours at 90°–110° F. in pits. After the lay (dwell) period, the fabric is dyed and then finished with softener with no additional cellulase treatment.

Example 9B repeats the same procedure as in Example 9A except that Rapidase GL is used in place of Cellusoft L and the lay time occurs in boxes.

Example 9C repeats the same procedure as in Example 9A except that the lay time occurs in J-boxes.

Fabric processed according to each of Examples 9A, 9B and 9C, perform acceptably for linting. No yellowing or significant strength loss is noted. Minimal lint is carried forth on the final product.

EXAMPLE 10

Each of the procedures of Example 9 is repeated with the following additions: in addition to the cellulase treatment during preparation, during finishing of the fabric is treated with 0.075–0.15% Cellusoft L on the weight of the fabric in addition to the softener solids. After finishing, the fabric lay time before drying ranges from 0 to 60 minutes. Drying temperature is 275°–325° F. in loop dryers for 15 to 30 minutes.

Fabrics processed in this maner have excellent linting performance and exceed the performance of the towels prepared according to examples 9A, 9B and 9C in each case. Further, no yellowing or notable strength loss was observed. Minimal lint was carried forth on the final product. The differences are visually apparent but cannot be quantified.

EXAMPLE 11

Each of the procedures of Example 9 is repeated with the following additions: the concentration of cellulase during preparation is reduced to 0.075–0.2% on the weight of the bath and on the weight of the towel (fabric). The temperature is 80°–110° F. The lay (dwell) time is increased to 4–16 hours.

Fabrics processed in this manner perform acceptably for linting with no yellowing or notable strength loss. Minimal lint is carried forth on the final product.

EXAMPLE 12

Any one of the procedures of Example 10 is repeated with the following changes: The cellulase added in the finishing stage on the weight of the towel is reduced to 0.035–0.10% and softener solids are 0.20–0.60% on the weight of the towel.

The towels exhibit excellent linting performance, no notable strength loss, no yellowing, and minimal lint carried forth on the final product.

EXAMPLE 13A and 13B

During the final washing of a dyed fabric prior to finishing, Cellusoft L is applied at a rate of 0.2–0.4% on the weight of the towel at 80°–130° F. at a pH in the range 4.8–5.3. Thereafter, the fabric is allowed to lay (dwell) 2–12 hours at 80°–100° F. and then finished in a conventional manner.

In Example 13B, the cellulase is applied at a concentration 0.075–0.2% on the weight of the towel at 80°–130° F. at a pH range of 4.8–5.3 and the towel is allowed to lay (dwell) for a longer period, i.e. 12–18 hours, at 80°–100° F.

Thereafter, the towels of both 13A and 13B are finished with no further cellulose treatment.

Towels treated by these procedures exhibit excellent linting performance and minimal lint is carried forth on the final product. Further, no yellowing and no noticable strength loss is observed.

EXAMPLE 14

The procedure of both Example 13A or 13B are repeated with the following changes: during finishing, the cellulose is applied at a lower rate, i.e. 0.035–0.15% on the weight of the towels along with softener solids of 0.2–0.6% on the weight of the towel. After finishing, lay (dwell) time ranges from 0–60 minutes before drying occurs at 275°–325° F. for 15–30 minutes in a hot forced air loop dryer.

The resulting towels exhbit excellent linting performance, no notable strength loss, no yellowing, and minimal lint carried forth on the final product.

EXAMPLE 15

After preparation, a fabric is readied for dyeing or finishing by adjusting the moisture across the fabric to a uniform level to promote finishing, drying, and or dyeing. Moisture level adjustment is typically handled by use of a double saturator squeeze roll or a single saturator squeeze roll set up where fabric is immersed in water (wet on wet) and squeezed to a uniform moisture level. Cellusoft L cellulase is applied at a concentration of 0.1–0.3% on the weight of the towel at a bath temperature of 80°–120° F. and at a pH of 4.8–5.3. The saturated fabric is allowed to lay (dwell) for various periods ranging from 0 to 60 minutes before drying. The fabric is slowly dried at 275°–325° F. over 15–30 minutes in a forced hot air loop dryer. The fabric is finished with no cellulase treatment.

Towels manufactured by this procedure exhibit excellent performance. No notable strength loss or yellowing is observed. Minimal lint is carried forth on the final product.

EXAMPLE 16

The procedure of Example 15 is repeated except that the towels are finished with a second cellulase treatment using 0.2–0.6% softener solids on the weight Of the towel and 0.075–0.2% Rapidase GL on the weight of the towel. Lay time after the finish chemicals application ranges from about 0 to 60 minutes before the fabric is dried at 275°–325° F. over 15 to 30 minutes in a hot, forced air, loop dryer.

The towels exhibit excellent linting performance, no notable strength loss, no yellowing, and minimal lint carried forth on the final product.

EXAMPLE 17

In Example 17, the procedure of Example 1 is repeated with the following changes: A 0.30% cellulase enzyme NOVO solution is prepared. During the desizing stage of a 100% Cotton Twill fabric is treated with the cellulase solution for 12 hours. The cellulase treatment solution temperature is 120°–130° F. and the fabric is maintained between 80°–90° F.

The fabric retains 92.4% of its strength and does not demonstrate any yellowing as compared to an identical fabric which is not cellulase treated. After one home laundering, fair to good linting performance is observed.

COMPARATIVE EXAMPLES

Cotton-comprising fabric as is generally described in the Examples above except with the variations in time, temperature, pH and concentration of cellulase enzyme as noted. Each fabric in the Comparative Examples failed the delinting, strength loss, and or yellowing performance requirements for commercial acceptability and thus represent conditions which were found incapable of adequately delinting the cotton fabrics, particularly without yellowing and strength loss.

COMPARATIVE EXAMPLE A

After preparation, a cotton fabric in open-width form is padded through a water mangle (pad) and squeezed to uniform moisture across the fabric. The fabric is then saturated with cellulase solution at 130° F. and a pH solution of 4.9 and 5.2. The cellulase solution is such that 1.5–3% Cellusoft L is added to the fabric (on the weight of the fabric). The pad solution of the Cellusoft L is at 10.0% on the weight of the bath and exchange is 15–30%. The saturated fabric is then immediately dried on steam heated cans with no dwell time and within 0.5–1.5 minutes. After drying, fabric is finished in a conventional manner and no cellulase is added in finishing.

Fabric processed in this manner exhibits substantial linting during a first wash and fails to be adequately delinted because of the extremely short reaction time due to the immediate and rapid deactivation of the cellulase by the steam heated drying cans.

COMPARATIVE EXAMPLE B

The procedure of Comparative Example A is repeated except that the finishing bath (with softener(s) and other conventional finishing agents) with 0.035–0.08% cellulase on the weight of the towel, applied by a combination of kiss coat finishing and dip nip (squeeze) finishing. The fabric is dried after finish application with a lay (dwell) time prior to drying ranging from 0 to 60 minutes Drying temperatures range from 275°–325° F. and drying time was from 15–30 minutes.

Fabric (towelling) processed in this manner shows some improved linting performance over that of Comparative Example A, but is still not acceptable compared to the fabric processed in accordance with the Examples above. It is believed that the failure is due to a low add-on of cellulase enzyme.

The above is repeated at considerably higher concentrations and is still unacceptable due to the excessive yellowing observed. No washing operation follows the procedure of this Comparative Example.

COMPARATIVE EXAMPLE C

The Procedure of Example 1 is repeated except that the cellulase solution is maintained at a temperature of 110°–130° F. and at a bath concentration of 0.25–0.35%. Cellusoft L on the weight of the towel is 0.2–0.4%. After saturation, the fabric is held in pits (bins) for 2–3 days at 90°–110° F.

The fabric strength is severely damaged. Most of it has to be destroyed, although some of the fabric has enough strength remaining to continue processing (i.e. completing its preparation, dyeing, finishing). The fabric that retains enough strength to be completely processed performs acceptably for low linting. However, the strength loss is excessive, particularly the fabric toward the bottom of the bins (longer time and more temperature retained).

COMPARATIVE EXAMPLE D

After preparation, a fabric is dyed and a cellulase solution is applied in the last wash box of the dye process. The solution temperature is 90°–130° F. and the pH range is 4.2–5.2. Rapidase GL is added in a concentration of 0.75–1.25% on weight of the fabric. The treated fabric is put into holding bins for 2–4 hours at 90°–110° F. A precheck of strength and or propensity to yellow indicates substantial yellowing and strength loss are occuring. Thus the fabric is pulled and separately washed to prevent further fabric damge. The washing substantially removes the enzyme through dilution. After washing, the fabric is finished.

Fabric performs acceptably well for linting, but shows a slight tendency to yellow and a substantial loss of strength. When compared to any of the Examples 1–17, towel processed following the procedure of Comparative Example D result in a larger, more notable amount of lint being carried with the final product to the consumer and on visual inspection showed excessive fiber loss and yellowing.

COMPARATIVE EXAMPLE E

The procedure of Example 12 is repeated except that the fabric is immersed in a finishing solution containing 4.0–5.0% softener solids and 0.8–1% Cellusoft L cellulase at 80°–130° F. and squeezed (nipped) to 15–30% exchange or 0.6–1.5% softener solids on the towel and 0.12–0.3% Cellusoft on the weight of the towel. The finished (wet) fabric is allowed to lay (dwell) in boxes at 80°–100° F. for 30–60 minutes and then dried at 275°–325° F. in a hot air loop dyer over 15 to 30 minutes.

The fabric performs well from a linting standpoint, but yellows to unacceptable extent with heat in the drying operation. No notable strength loss is observed.

When compared to any of the Examples 1–17, towels processed following the procedure of Comparative Example E results in a larger, more noticable amount of lint being carried on the final product (towel) to the consumer and on visual inspection show exessive fiber loss.

COMPARATIVE EXAMPLE F

The procedure of Example 12 is repeated except that the finish softener solids are 2–4% on weight of the bath and either Cellusoft L or Rapidase GL at 0.75–1.25% on weight of bath and a 15–30% exchange.

Comparative Example F is run several times substituting concentrations of 0.3–0.6% softener solids with 0.11–0.19% cellulase and 0.6–1.2% softener solids with 0.22–0.38% cellulase on the weight of the fabric.

Towels processed by following the procedures of all the Examples in F exhibit excessive yellowing, particularly on pastel shades. While linting performance alone is acceptable and no notable strength loss is observed, the yellowing that occurs makes these conditions unacceptable.

When compared to any of the Examples 1–17, towels processed following the procedure of Comparative Example F result in a larger, more noticable amount of lint being on the final product (towel) to the consumer and on visual examination show excessive fiber loss.

COMPARATIVE EXAMPLE G

The procedure of example 17 except that a cellulase solution of 0.60% is prepared. The solution is applied to a fabric and held for 12.0 hours. The treatment solution temperature is between 120°–130° F., and the dwell temperature is 80°–90° F. Further, the pH of the solution is between 4.8 and 5.3.

The fabric retains 90.60% of its strength, demonstrates the linting performance is good. The fabric, however, upon visual inspection is substantially yellower than an untreated fabric.

COMPARATIVE EXAMPLE H

A 100% cotton twill fabric is saturated with water. No cellulase is applied. The saturated fabric is held for 12 hours. The treatment solution temperature is between 120°–130° F., and the dwell temperature is 80°–90° F. Further, the pH of the solution is between 4.8 and 5.3.

The fabric retains 100% of its strength. After one home laundering, however linting performance is poor to fair.

COMPARATIVE EXAMPLE I

The procedure of Example 17 except that a cellulase solution of 0.03% is prepared. The solution is applied to the fabric and held for 12 hours. The treatment solution temperature is between 120°–130° F., and the dwell temperature is 80°–90° F. Further, the pH of the solution is between 4.8 and 5.3.

The fabric retains 96.8% of its strength. The towel delinting, however, is poor to fair after one wash. The fabric does not yellow.

COMPARATIVE EXAMPLE J

The procedure of Example 17 is performed except that the solution is applied to a cotton fabric and held for 1.0 hour. The treatment solution temperature is between 120°–130° F., and the dwell temperature is 80°–90° F. Further, the pH of the solution is between 4.8 and 5.3.

The fabric retains 98.8% of its strength, and does not yellow. The fabric, however, demonstrates poor to fair linting performance after one wash.

COMPARATIVE EXAMPLE K

No cellulase solution is prepared or applied. Instead, a solution of a 2.5% OWF cationic softener Discosoft 1523 is prepared. The softener is applied to a cotton twill fabric and held for 12 hours. The treatment solution temperature is between 120°–130° F., and the dwell temperature is 80°–90° F. The pH of the solution is between 4.8 and 5.3.

The fabric retains only 87.24% of its strength. The towel delinting after one wash is poor, but the fabric is not yellowed.

COMPARATIVE EXAMPLE L

The procedure of Example 17 is performed except that 2.50% of Discosoft 1523 softener is added. The fabric is treated for 12 hours.

While the linting performance of the fabric is good to excellent, the fabric yellows substantially and retains only 79.30% of its strength.

What is claimed is:

1. A process for selectively removing embedded lint precursors with a cellulase enzyme during a continuous manufacturing process, having at least formation, preparation, dyeing, and finishing steps, for an open end cotton fabric, untreated with a swelling agent, comprising the steps of:

(a) preparing at least one aqueous cellulase solution comprising cellulase and a nonionic surfactant;

(b) continually adding the at least one cellulase solution, in a step of the process, in a fixed, limited path, with no substantial agitation or recirculation, in an amount and under conditions sufficient for hydrolyzing embedded lint precursors, to the open end cotton fabric comprising digestible cellulosic fibrils and non-digestible cellulosic fibrils, the digestible cellulosic fibrils being embedded lint precursors within the path travelled by the cellulase, and the nondigestable cellulosic fibrils being located outside the path travelled by the cellulase; and (c) removing the embedded lint precursors by cellulase digestion of the embedded lint precursors.

2. The process of claim 1, wherein the fabric is to be saturated with water in a stage of the manufacturing process after the formation step.

3. The process of claim 1, wherein the pH of the cellulase aqueous solution will substantially maximize activity of the cellulase enzyme.

4. The process of claim 1, wherein the at least one cellulase solution is applied immediately prior to a holding period in the preparation step of the continuous manufacturing process.

5. The process of claim 4, wherein the holding period is immediately followed by a contacting of the fabric with water.

6. The process of claim 4, wherein the holding period is immediately followed by a drying of the fabric by exposure to heat above 200° F.

7. The process of claim 1, further comprising deactivation of the cellulase enzyme after the digestible fibrils have been digested.

8. The process of claim 1, further comprising removing the cellulase enzyme and digested products thereof after the digestible fibrils have been digested.

9. The process of claim 1, wherein the at least one cellulase solution is added before a washing step in the manufacturing process.

10. The process of claim 1, wherein the pH of the cellulase solution is about 3.8 to 8.

11. The process of claim 1, wherein the conditions include a temperature of about 60° to about 130° F.

12. The process of claim 1, wherein the cellulase is in contact with the fabric for a period of up to 4 days.

13. The process of claim 1, wherein the at least one cellulase solution has a concentration between about 0.1 to 0.6% by weight, a solution temperature between 120° and 130° F., and a pH of about 4.8 to 5.3.

14. The process of claim 1, wherein the amount of cellulase added is about 0.05 to 0.5% based on the weight of the fabric.

15. The process of claim 1, wherein a first cellulase solution and a second cellulase solution are applied during the manufacturing process, wherein the second solution has a lower cellulase concentration than that of the first solution and the second solution is added in the process after addition of the first solution.

16. The process of claim 15, wherein the first and second cellulase solutions are added during a desizing step and the finishing step, respectively; the cellulase solution added during the finishing step containing about 5 to 33% of the total cellulase enzyme added.

* * * * *